US012622807B2

(12) United States Patent
Asano et al.

(10) Patent No.: US 12,622,807 B2
(45) Date of Patent: May 12, 2026

(54) AURICLE HEATING DEVICE

(71) Applicant: KOBAYASHI PHARMACEUTICAL CO., LTD., Osaka (JP)

(72) Inventors: Ryota Asano, Ibaraki (JP); Yuji Sekido, Ibaraki (JP); Yoshihiro Ujihara, Ibaraki (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 470 days.

(21) Appl. No.: 18/002,708

(22) PCT Filed: Jun. 15, 2021

(86) PCT No.: PCT/JP2021/022761
§ 371 (c)(1),
(2) Date: Dec. 21, 2022

(87) PCT Pub. No.: WO2022/004365
PCT Pub. Date: Jan. 6, 2022

(65) Prior Publication Data
US 2023/0233369 A1 Jul. 27, 2023

(30) Foreign Application Priority Data

Jun. 30, 2020 (JP) ................................. 2020-113555

(51) Int. Cl.
*A61F 7/03* (2006.01)
*A61F 7/00* (2006.01)
*A61F 7/02* (2006.01)

(52) U.S. Cl.
CPC ........ *A61F 7/03* (2013.01); *A61F 2007/0005* (2013.01); *A61F 2007/0225* (2013.01)

(58) Field of Classification Search
CPC ...... A61F 2007/0005; A61F 2007/0225; A61F 7/03
See application file for complete search history.

(56) References Cited

U.S. PATENT DOCUMENTS

2013/0079851 A1 3/2013 Tagami et al.
2015/0215693 A1* 7/2015 Sandanger ........... H04R 1/1083
381/380

(Continued)

FOREIGN PATENT DOCUMENTS

CN 102869326 B 4/2017
CN 107714283 A 2/2018

(Continued)

OTHER PUBLICATIONS

Extended European Search Report issued in European Appln. No. 21832259.2 mailed Jul. 3, 2024.

(Continued)

*Primary Examiner* — Joseph A Stoklosa
(74) *Attorney, Agent, or Firm* — ROSSI, KIMMS & McDOWELL LLP

(57) ABSTRACT

An auricle heating device according to one aspect of the present invention, including a pair of left and right heating devices that are to be respectively worn in a left and right ear, wherein each heating device includes: a heating body; a holding portion configured to hold the heating body; and a fixing portion. The fixing portion is connected to the holding portion and configured to be worn in an auricle so as to fix the holding portion so as to be in contact with an inner side of the auricle. The left and right heating devices are separate from each other.

19 Claims, 13 Drawing Sheets

1a (1b)

(56)  References Cited

U.S. PATENT DOCUMENTS

| | | | |
|---|---|---|---|
| 2017/0041701 A1* | 2/2017 | Cheng | H04R 1/105 |
| 2017/0195771 A1* | 7/2017 | Hung | G06F 3/165 |
| 2018/0270558 A1* | 9/2018 | Ring | H04R 1/1075 |
| 2025/0016486 A1* | 1/2025 | Kon | H04R 1/1075 |

FOREIGN PATENT DOCUMENTS

| | | | |
|---|---|---|---|
| CN | 110505855 A | | 11/2019 |
| JP | 2006320363 | * | 11/2006 |
| JP | 2006320363 A | | 11/2006 |
| JP | 2014076159 A | | 5/2014 |
| JP | 2018086202 A | | 6/2018 |
| KR | 1020190080614 A | | 7/2019 |

OTHER PUBLICATIONS

Office Action issued in Japanese Appln. No. 2020-113555 mailed Aug. 8, 2023. English machine translation provided.
International Search Report issued in Intl. Appln. No. PCT/JP2021/022761 mailed Jul. 13, 2021. English translation provided.
Written Opinion issued in Intl. Appln. No. PCT/JP2021/022761 mailed Jul. 13, 2021.
Office Action issued in Taiwanese Appln. No. 110121981 on Jun. 25, 2024. English machine translation provided.
First Office Action issued in Chinese Appln. No. 202180003652.9 mailed on Feb. 13, 2026. English machine translation provided.

* cited by examiner

1

1a (1b)

121

VAS1

Not warm ———————————— Warm

VAS2

Not comfortable ———————————— Comfortable

AURICLE HEATING DEVICE

TECHNICAL FIELD

The present invention relates to an auricle heating device.

BACKGROUND ART

Patent Literature 1 discloses an ear heating device that is shaped as a pouch having an opening for insertion of the ear, has a heat generating function, and covers a portion or the entirety of the ear. Patent Literature 2 discloses an ear canal temperature adjustment device that is provided with an ear canal insertion portion that is to be inserted into an ear canal, and a temperature adjustment portion, and the ear insertion portion includes a detachable heat storing portion and an insertion portion main body. The user of the of the ear canal temperature adjustment device can detach the heat storing portion from the insertion portion main body, heat or cool the heat storing portion with use of the temperature adjustment portion, and then attach the heat storing portion to the insertion portion main body for usage.

CITATION LIST

Patent Literature

Patent Literature 1: JP 2018-086202A
Patent Literature 2: JP 2014-076159A

SUMMARY OF INVENTION

Technical Problem

The ear heating device disclosed in Patent Literature 1 is worn so as to cover the ear with the intention of heating surrounding portions of the ear including the base portion of the ear. Thus, there may be cases where it is difficult to adjust the position of the portion including the heat generating function depending on the posture of the user. Also, the ear canal temperature adjustment device disclosed in Patent Literature 2 is configured such that a pair of ear canal insertion portions are connected by a connection portion, and the ear canal insertion portions are respectively inserted into two ears with the connection portion placed on the back of the neck. Thus, the posture of the user during usage is limited.

An object of the present invention is to provide an auricle heating device that has excellent fixability to a user's auricle, and can be used in a wide-range of postures taken by the user.

Solution to Problem

An auricle heating device according to one aspect of the present invention, including a pair of left and right heating devices that are to be respectively worn in a left and right ear, wherein each heating device includes: a heating body; a holding portion configured to hold the heating body; and a fixing portion. The fixing portion is connected to the holding portion and configured to be worn in an auricle so as to fix the holding portion so as to be in contact with an inner side of the auricle at a predetermined position. The left and right heating devices are separate from each other.

The auricle heating device according to the one aspect, wherein, in each heating device, the fixing portion may be worn in the auricle such that the holding portion is fixed so as to be in contact with an inner wall surface near a cavum conchae.

The auricle heating device according to the one aspect, wherein, in each heating device, the holding portion may include a supporting portion configured to come in contact with the inner wall surface of the cavum conchae located near an antitragus, and support fixing realized by the fixing portion.

The auricle heating device according to the one aspect, wherein, in each heating device, the holding portion may include a contact surface portion that includes a contact surface configured to come into contact with the inner side of the auricle at a predetermined position, and a side wall portion that stands upright from a circumferential edge of the contact surface portion, and the heating body may be fitted into the side wall portion from a back surface side of the contact surface and held by the heating body.

The auricle heating device according to the one aspect, wherein, in each heating device, the fixing portion may include an insertion portion configured to be inserted to a shallow portion of an external acoustic meatus hole while being in intimate contact with an inner wall surface of the external acoustic meatus hole.

The auricle heating device according to the one aspect, wherein, in each heating device, the insertion portion may be configured to close off the external acoustic meatus hole and block out external audio.

The auricle heating device according to the one aspect, wherein, in each heating device, the fixing portion may include a first extension portion that extends from the holding portion and is configured to reach an inner wall surface of a cymba conchae, and the first extension portion and the supporting portion may be configured to press against the inner side of the auricle while the first extension portion uses the inner wall surface of the cymba conchae as a support portion and the supporting portion uses the inner wall surface of the cavum conchae located near the antitragus as a support portion.

The auricle heating device according to the one aspect, wherein, in each heating device, the fixing portion may include a second extension portion that extends from the holding portion and is configured to reach a first position that is on an inner wall surface of a cavum conchae and that is located inward of an antihelix, and the insertion portion and the second extension portion may be configured to press against the inner side of the auricle while the insertion portion uses the inner wall surface of the external acoustic meatus hole as a support portion and the second extension portion uses the first position as a support portion.

The auricle heating device according to the one aspect, wherein, in each heating device, the fixing portion may include a hooking portion that is to be hooked to an intertragic notch.

The auricle heating device according to the one aspect, wherein, in each heating device, the heating body may generate heat using a chemical reaction.

The auricle heating device according to the one aspect, in each heating device, the chemical reaction may include a metal oxidation reaction.

The auricle heating device according to the one aspect, wherein, in each heating device, the heating body may be a disposable component.

The auricle heating device according to the one aspect, wherein, in each heating device, at least one of the holding portion and the fixing portion may be made of at least one of rubber, elastomer, and a synthetic resin.

The auricle heating device according to the one aspect, wherein, in each heating device, at least one of the holding portion and the fixing portion may be made of at least one of rubber mixed with a metal, rubber mixed with carbon, an elastomer mixed with a metal, an elastomer mixed with carbon, a synthetic resin mixed with a metal, a synthetic resin mixed with carbon, and a thermally conductive resin.

Advantageous Effects of the Invention

With the auricle heating device according to the one aspect, the holding portion holding the heating body is fixed so as to be in contact with the inner side of the auricle, and thus the heating body can be more easily positioned relative to the auricle of the user, and discomfort felt when the auricle heating device is worn is reduced. Also, with the auricle heating device according to the one aspect, the left and right heating devices are separated from each other, and thus the posture of the user is not impaired by a connection portion that connects the pair of heating devices, and the auricle heating device can also be used while the user is lying down, for example.

DESCRIPTION OF EMBODIMENTS

An auricle heating device according to one embodiment of the present invention is described below with reference to the drawings.

1. Overall Configuration

Figure 1:
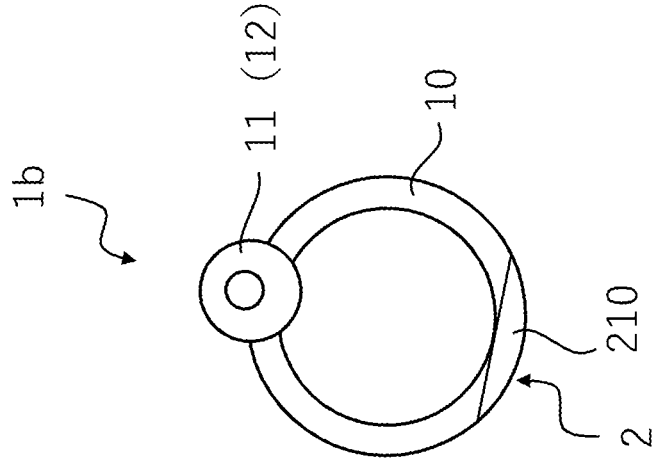
FIG. 1 is a top view of an auricle heating device according to one embodiment.
Figure 1:
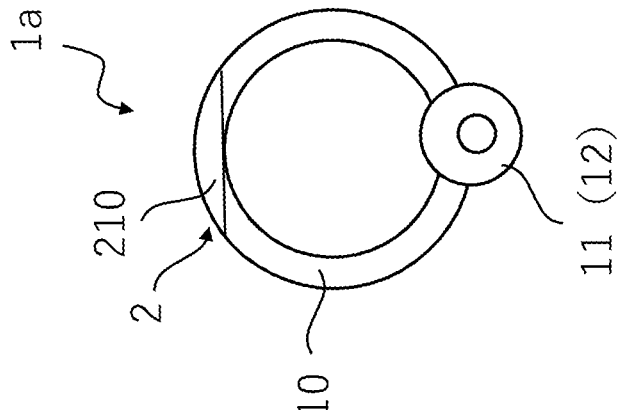

FIG. 1 is a top view of an auricle heating device 1 according to one embodiment of the present invention. The auricle heating device 1 according to the present embodiment includes a pair of heating devices 1a and 1b that are separated from one another. The pair of heating devices 1a and 1b are respectively worn in the left and right ears and used to heat the corresponding auricle. The pair of heating devices 1a and 1b may be configured in the same manner apart from having shapes that are mirror opposites of each other, or may be configured so as to have the same shape without any particular distinction between the left and right devices. The pair of heating devices 1a and 1b according to the present embodiment have the same configuration without any distinction made between left and right heating devices. Accordingly, only the configuration of the heating device 1a is described below for the sake of brevity. Note that, the "top surface" side of the auricle heating device 1 is the side that comes in contact with the inner side of the auricle when the auricle heating device 1 is worn in the auricle, and a side surface and bottom surface of the auricle heating device 1 are defined in reference to this.

Figure 2:
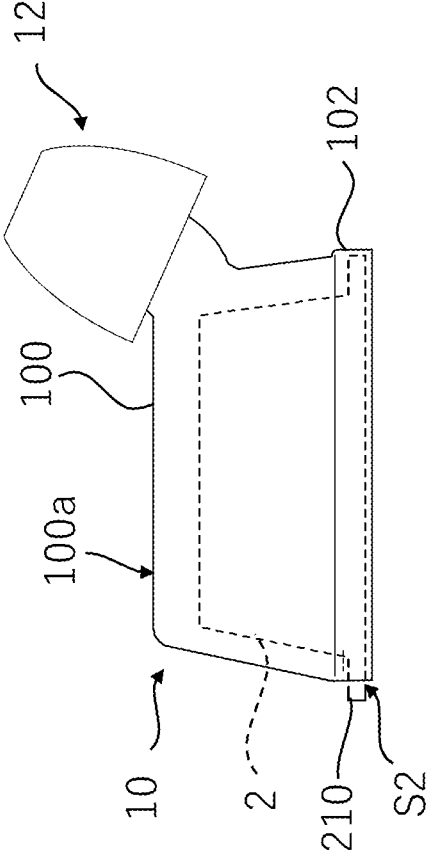
FIG. 2 is a side view of the auricle heating device according to one embodiment.
Figure 6:
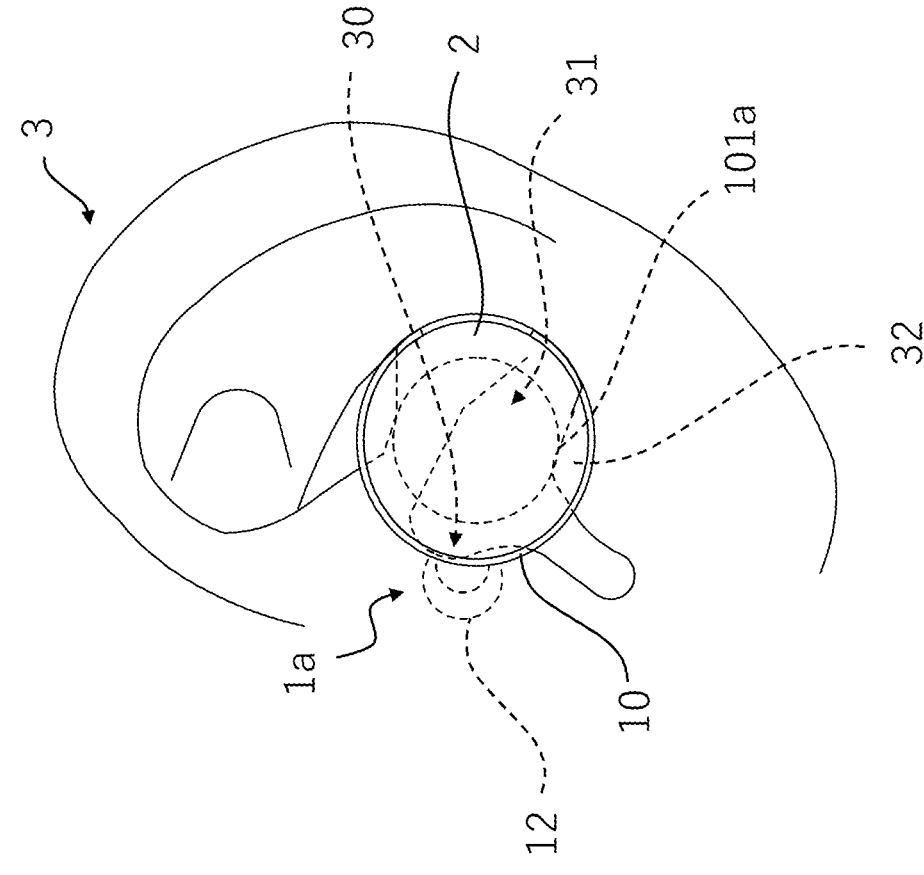
FIG. 6 is a diagram showing a usage state of the auricle heating device according to one embodiment of the present invention.

FIG. 2 is a side view of the heating device 1a. As shown in FIGS. 1 and 2, the heating device 1a is provided with a heating body 2, a holding portion 10, and a fixing portion 11. The holding portion 10 is configured so as to detachably hold the heating body 2. The fixing portion 11 is connected to the holding portion 10, and configured to fix the holding portion 10 holding the heating body 2 so as to be in contact with the inside of the auricle 3 at a predetermined position. The fixing portion 11 according to the present embodiment includes an insertion portion 12 that is inserted to a shallow portion of an external acoustic meatus hole 30 (see FIG. 6) while being in intimate contact with the inner wall surface of the external acoustic meatus hole 30. The insertion portion 12 is configured to close off the eternal acoustic meatus hole 30, and block out external audio. In other words, the auricle heating device 1 according to the present embodiment also functions as an ear plug.

2. Configuration of Each Portion

<2-1. Heating Body>

Figure 3:
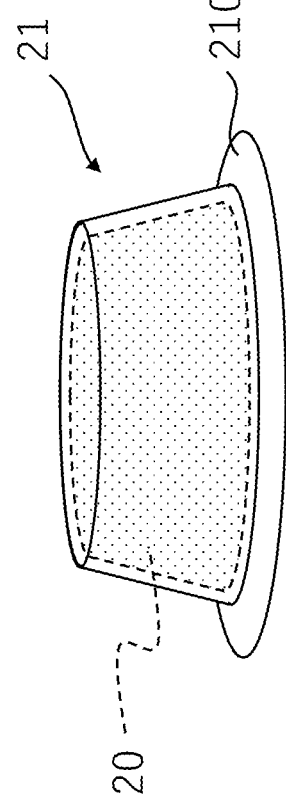
FIG. 3 is a perspective view of a heating body.

FIG. 3 is a perspective view of the heating body 2. The heating body 2 is a typical disposable heat pad, and is sealed in a film pouch (not shown) for keeping out air prior to use. The heating body 2 includes a heat generating composite 20 that undergoes a chemical reaction in which heat is generated when exposed to air, and a containing portion 21 that contains the heat generating composite 20. The heat generating composite 20 may be a powder body including, for example, a metal powder such as iron powder, water, a water retaining material, or the like, and the chemical reaction may be an oxidation reaction of a metal such as iron. The containing portion 21 has a hollow truncated cone shape, and is provided with a flange portion 210 at the circumferential edge portion of the end surface with the larger diameter. The heat generating composite 20 is contained in the internal space of the containing portion 21. The containing portion 21 may be made of a material with air permeability, or a material provided with air holes as needed. Examples of the material forming the containing portion 21 include non-woven fabric, a synthetic resin, rubber, an elastomer, fabric, and the like, and the containing portion 21 according to the present embodiment is made of a non-woven fabric. It is preferable that these materials are appropriately processed so as to maintain a certain shape in order to maintain a state in which the heating body 2 is housed in the holding portion 10.

When the auricle heating device 1 is to be used, the heating body 2 is taken out of a film pouch that keeps air out, and is fitted into the holding portion 10 such that the flange portion 210 is located on a later-described open end side of the holding portion 10. When the auricle heating device 1 is being used, the open end of the holding portion 10 is located on the side distanced from an auricle 3, and a closed end of the holding portion 10 that is closed off by a later-described contact surface portion 100 is located on the side near the auricle 3. That is, when the auricle heating device 1 is in the usage state shown in FIG. 6, the externally visible portion is mostly the end surface on the large-diameter side of the containing portion 21 and the flange portion 210 (see FIG. 6). In this way, as a result of the heating body 2 having a surface not covered by the holding portion 10, the heat generating composite 20 is likely to be exposed to air via the containing portion 21, and the chemical reaction of the heat generating composite 20 is promoted, and thus heat is efficiently generated.

<2-2. Holding Portion>

Figure 4:
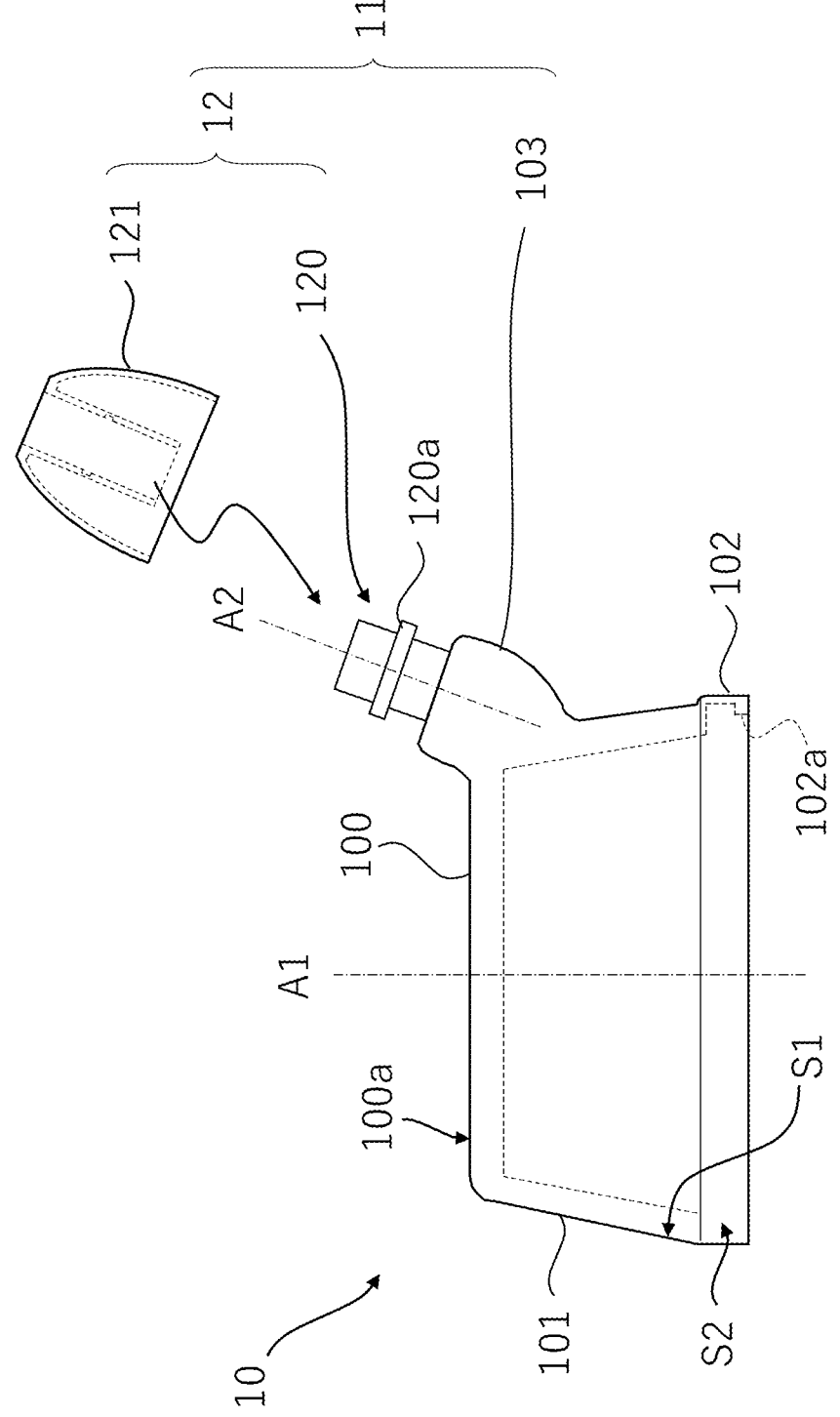
FIG. 4 is an exploded side view of a holding portion and a fixing portion.

FIG. 4 is an exploded side view of the holding portion 10 and the fixing portion 11. The holding portion 10 according to the present embodiment has a substantially truncated cone shape, and includes the contact surface portion 100 and a side wall portion 101. The contact surface portion 100 is provided at the end portion of the substantially truncated cone shape with the smaller diameter, and includes a substantially circular contact surface 100a that comes into contact with the auricle 3 at a predetermined position thereof when the heating device 1a is worn in the auricle 3. In view of increasing an effect realized by heat from the heating body 2, it is preferable that the contact surface 100a comes into contact with the inner wall surface of a cavum conchae 31, and in the heating device 1a according to the present embodiment, a configuration is employed where most of the contact surface 100a comes into contact with the inner wall surface of the cavum conchae 31.

The side wall portion 101 stands upright from a circumferential edge of the contact surface portion 100 in a direction opposite to the direction in which the contact surface 100a is oriented, and is a portion that extends with an increasing diameter and forms a circumferential side surface of a substantially truncated cone. The end portion of the substantially truncated cone shape with the larger diameter is open, and thus the side wall portion 101 and the contact surface portion 100 form a space S1 of which one side is open. The space S1 is formed to be approximately as large as or slightly larger than the heating body 2, and the heating body 2 can be fitted therein via the one side opening with the flange portion 210 brought to the front. When the heating body 2 is fitted into the space S1, the heating body 2 enters a state where it is mostly covered by the holding portion 10 and is housed in the holding portion 10.

The holding portion 10 also includes a large diameter portion 102 that is continuous with the side wall portion 101, receives the flange portion 210 of the heating body 2, and covers the flange portion 210 from the outside in a radial direction. The large diameter portion 102 is a ring-shaped portion that is integrated with the side wall portion 101 at the end portion of the side wall portion 101 with the larger diameter. The large diameter portion 102 has a rib 102a that protrudes inward in the radial direction from the inner circumferential surface of the end portion on the side opposite to where the rib 102a is formed. Excluding the portion where the rib 102a is formed, the inner diameter of the large diameter portion 102 is slightly larger than the outer diameter of the flange portion 210, and the portion where the rib

102a is formed has a smaller inner diameter than the outer diameter of the flange portion 210. When the flange portion 210 is fitted into the large diameter portion 102 so as to be located on the contact surface portion 100 side of the rib 102a, the heating body 2 is unlikely to come loose from the holding portion 10 due to the provision of the rib 102a, and is held by the holding portion 10. Accordingly, the holding portion 10 can hold the heating body 2 even if it is not provided with a closing/opening function for opening and closing the space S1. Also, the circumferential edge portion of the flange portion 210 is covered by the large diameter portion 102, and discomfort caused by contact between the flange portion 210 and the auricle when wearing the auricle heating device 1 is suppressed. Note that, in view of facilitating attachment/detachment of the heating body 2, a notch S2 formed by cutting out a portion in the circumferential direction of the large diameter portion 102 may be provided. FIGS. 1 and 2 show a state where a portion of the flange portion 210 is visible from outside of the holding portion 10 through the notch S2.

The holding portion 10 is configured so that, in a state where the heating device 1a is worn in the auricle 3, a portion of the side wall portion 101 comes into contact with the inner wall surface of the cavum conchae 31 located near the antitragus. Thus, the entirety of the heating device 1a is supported by a portion of the side wall portion 101 and is stable in the auricle 3. In other words, the portion of the side wall portion 101 that comes into contact with the inner wall surface of the cavum conchae 31 located near an antitragus 32 functions as a supporting portion 101a that supports fixing realized by the fixing portion 11 (see FIG. 6). When the heating device 1a worn in the auricle 3 is seen from outside the auricle 3, the supporting portion 101a is located at substantially 6 o'clock, assuming that the insertion portion 12 is located at 9 o'clock, for example.

In the present embodiment, the holding portion 10 is made of a flexible material, and can deform during attachment and detachment of the heating body 2. Thus, attachment and detachment of heating body 2 is made easier for the user of the auricle heating device 1, the holding portion 10 matches the shape of the heating body 2, and the heating body 2 fitted into the space S1 is unlikely to come loose from the holding portion 10. Also, when coming into contact with the auricle 3, the holding portion 10 can deform so as to match the uneven structure of the auricle 3, including the angle of a later-described connection portion 103, and thus the user is unlikely to feel discomfort when wearing the heating device 1a.

The material of the holding portion 10 is not particularly limited, but examples of the material include rubber, elastomer, synthetic resins including soft resin and hard resin, and the like. More specifically, examples include polypropylene (PP), polyethylene (PE), polyethylene terephthalate (PET), elastomer, and the like. In view of efficiently transferring heat from the heating body 2 to the auricle 3, the material of the holding portion 10 may be a material with high thermal conductivity. Examples of such a material include materials with enhanced thermal conductivity obtained by mixing a base material such as rubber, an elastomer, or a synthetic resin, with a material with high thermal conductivity such as metal or carbon, and a thermally conductive resin. Note that, thermally conductive resin is a resin with high thermal conductivity.

<2-3. Fixing Portion>

The fixing portion 11 positions and holds the holding portion 10 at a predetermined position inside the auricle 3.

Thus, the entire heating device 1a is fixed to the auricle 3 of the user, and is unlikely to shift and come loose.

The fixing portion 11 is formed as one piece with the contact surface portion 100 and the side wall portion 101, and includes the connection portion 103 that extends from the contact surface portion 100 and the side wall portion 101, a first insertion portion 120 that is continuous with the connection portion 103, and a second insertion portion 121. In the present embodiment, the connection portion 103 and the first insertion portion 120 are formed as one piece, and the first insertion portion 120 and the second insertion portion 121 are formed separate from each other. The connection portion 103 has a solid, substantially columnar shape whose central axis is curved. The first insertion portion 120 has a solid, substantially columnar shape, and is formed such that a central axis A2 thereof is inclined at a predetermined angle from a central axis A1 of the substantially truncated cone of the holding portion 10. An annular rib 120a is provided on the circumferential side surface of the first insertion portion 120. As described below, the rib 120a is configured to be fitted into a groove portion 121a of the second insertion portion 121, with which the second insertion portion 121 is fixed to the first insertion portion 120. The first insertion portion 120 and the second insertion portion 121 together form the insertion portion 12. That is, the holding portion 10 and the insertion portion 12 are connected by the connection portion 103. The second insertion portion 121 is made of a flexible material, and is configured so as to, upon insertion to a shallow portion of the external acoustic meatus hole 30, deform so as to match the inner wall surface of the external acoustic meatus hole 30 and come into intimate contact with the inner wall surface of the external acoustic meatus hole 30.

Figure 5:
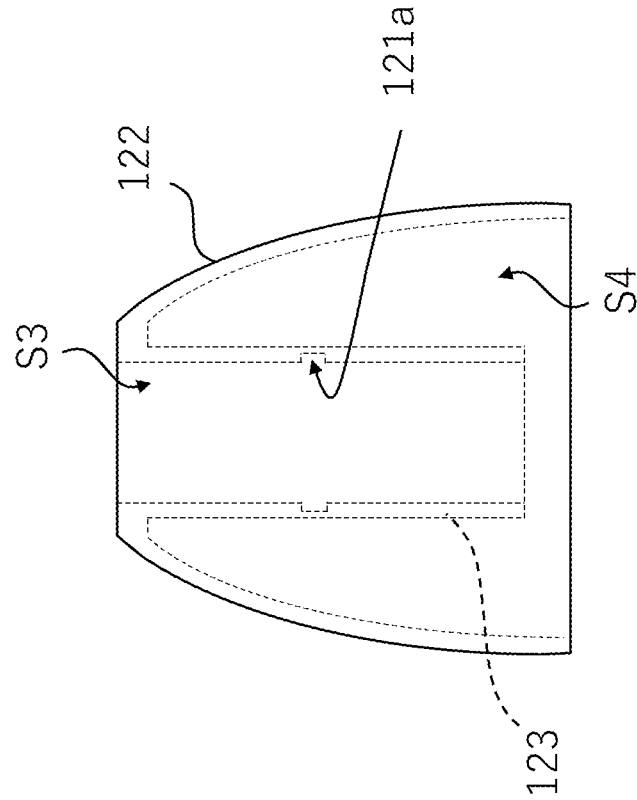
FIG. 5 is a side view of a second insertion portion.

FIG. 5 is a side view showing the internal structure of the second insertion portion 121. The second insertion portion 121 is substantially shaped as a truncated cone whose circumferential side surface bulges outward as seen from the outside. The second insertion portion 121 includes an externally visible outer portion 122 that forms the circumferential side surface of a substantially truncated cone, and a non-externally visible inner portion 123 located inward of the outer portion 122 in the radial direction The inner portion 123 is the portion to which the first insertion portion 120 is fixed, and has a substantially cylindrical shape provided with a through hole S3 extending in the axial direction thereof. The inner diameter of the through hole S3 is made slightly larger than the outer diameter of the first insertion portion 120. The inner circumferential surface of the inner portion 123 is provided with the annular groove portion 121a, and the groove portion 121a is sufficiently large for the rib 120a of the first insertion portion 120 to be fitted therein. When the first insertion portion 120 is inserted into the through hole S3 of the inner portion 123, and at least either the inner portion 123 or the rib 120a is elastically deformed and fitted into the groove portion 121a, the through hole S3 of the second insertion portion 121 is filled by the first insertion portion 120, and the insertion portion 12 that blocks out external audio is formed.

The outer portion 122 is a portion that comes into contact with the inner wall surface of the external acoustic meatus hole 30. The end portion of the outer portion 122 with the smaller diameter is integrally continuous with the leading end portion on one side of the inner portion 123, and covers the entire inner portion 123 from the outside in the radial direction. There is a gap between the inner circumferential surface of the outer portion 122 and the outer circumferential surface of the inner portion 123 that forms a space S4.

Due to the space S4, when the insertion portion 12 is inserted into the external acoustic meatus hole 30, the outer portion 122 can easily deform so as to match the size and shape of the inner wall surface of the external acoustic meatus hole 30. Thus, the fixability of the heating device 1a to the auricle 3 is increased, and the heating device 1a can be suitably used as an ear plug.

The material of the second insertion portion 121 is not particularly limited, but examples of the material include rubber, elastomer, synthetic resins including soft resin and hard resin, and the like. More specifically, examples include polypropylene (PP), polyethylene (PE), polyethylene terephthalate (PET), elastomer, and the like. Note that, while the outer portion 122 and the inner portion 123 are formed as one piece, they may be made of different materials. Also, the material of the second insertion portion 121 may be a material obtained by mixing a base material such as rubber, an elastomer, or a synthetic resin with a material mixed with metal, carbon, or the like, and a thermally conductive resin.

3. Features

In the auricle heating device 1 according to the embodiment, the heating devices 1a and 1b worn in the left and right auricles 3 are formed separately. Thus, the user can use the auricle heating device 1 even when they are lying down. Also, the auricle heating device 1 according to the embodiment can heat the auricle 3 while also simultaneously functioning as an ear plug, and thus is particularly suited to use during sleep.

In the auricle heating device 1 according to the above embodiment, the holding portion 10 is fixed so as to particularly be in contact with the inner wall surface of the cavum conchae 31. As described below, the user feels more warmth and comfort when mainly the cavum conchae 31 is heated as opposed to when another portion of the auricle 3 is mainly heated. Thus, with the auricle heating device 1 according to the embodiment, a greater heating effect can be perceived.

In the auricle heating device 1 according to the embodiment, the fixing portion 11 is configured to be positioned inside the auricle 3 in addition to the holding portion 10. Thus, the user is unlikely to feel discomfort caused by wearing the heating devices 1a and 1b. Also, aesthetical changes during use are reduced compared to a case where a heating device is worn so as to cover the auricle 3 from the outside of the auricle 3, and thus the user is unlikely to feel displeasure in using the auricle heating device 1.

4. Variations

An embodiment of the present invention has thus been described, but the present invention is not to be limited to the aforementioned embodiment, and various changes can be made provided they do not depart from the gist of the present invention. For example, the following changes can be made. Also, the content of the following variations can be combined as appropriate.
<4-1>
The outer portion 122 and the inner portion 123 of the second insertion portion 121 may be formed separately, and for example, the outer portion 122 may be configured as a cover that is to be attached to the inner portion 123. Also, the insertion portion 12 may be formed by, for example, attaching a pad made of soft resin that comes into contact with the inner wall surface of the external acoustic meatus hole 30 to a main body portion made of a hard resin.

<4-2>

The holding portion 10 may be formed such that the end portion of the substantially truncated cone with the larger diameter is closed off, and, for example, an opening for fitting the heating body 2 is provided in the side wall portion 101. Also, the holding portion 10 may have a lid portion that can close off the space S1 at the end portion of the substantially truncated cone with the larger diameter. The shape of the heating body 2 may also be changed as appropriate depending on the shape of the holding portion 10, the position of the opening for fitting the heating body 2, and the like, and the flange portion 210 may be omitted, for example.

<4-3>

Figures 7A, 7B:
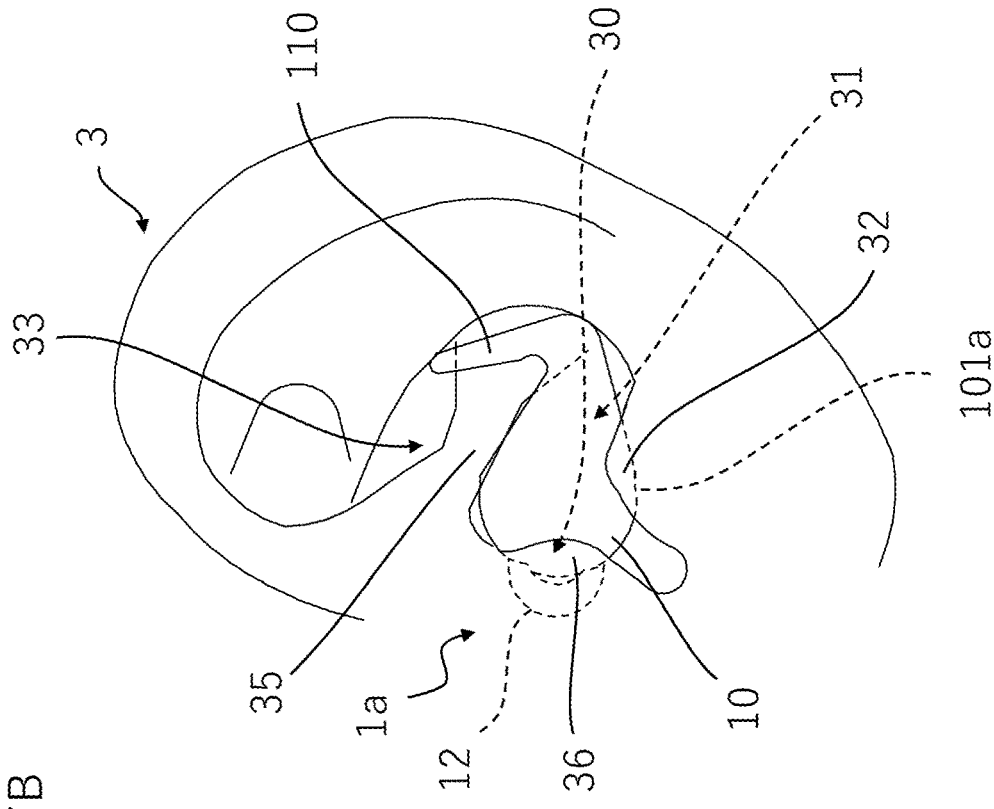
FIG. 7A is a side view of an auricle heating device according to a variation.
FIG. 7B is a diagram showing a usage state of the auricle heating device according to the variation.

The configurations of the holding portion 10 and the fixing portion 11 are not limited to those of the embodiment and can be changed as appropriate. For example, the fixing portion 11 may include a first extension portion 110 extending from the holding portion 10, in place of or in addition to the insertion portion 12. FIG. 7A is a side view of a heating device 1a according to such a variation, and FIG. 7B is a diagram showing the usage state of the heating device 1a shown in FIG. 7A. As shown in FIG. 7B, the first extension portion 110 extends from the holding portion 10, straddles a crus helicis 35, and reaches the inner wall surface of a cymba conchae 33. The first extension portion 110 and the supporting portion 101a are configured to press against the inner side of the auricle 3 while the first extension portion 110 uses the inner wall surface of the cymba conchae 33 as a support portion, and the supporting portion 101a of the holding portion 10 uses the inner wall surface of the cavum conchae 31 located near the antitragus 32 as a support portion. Thus, the holding portion 10 is reliably fixed so as to be in contact with the inside of the auricle 3, preferably the cavum conchae 31. Note that, as shown in FIG. 7B, the holding portion 10 may be configured to be positioned inward of the antitragus 32 and inward of an antilobium 36. The heating body 2 is not shown in FIG. 7, but as described above, the shape of and the method of housing the heating body 2 in the holding portion 10 may be selected as necessary.

<4-4>

Figures 8A, 8B:
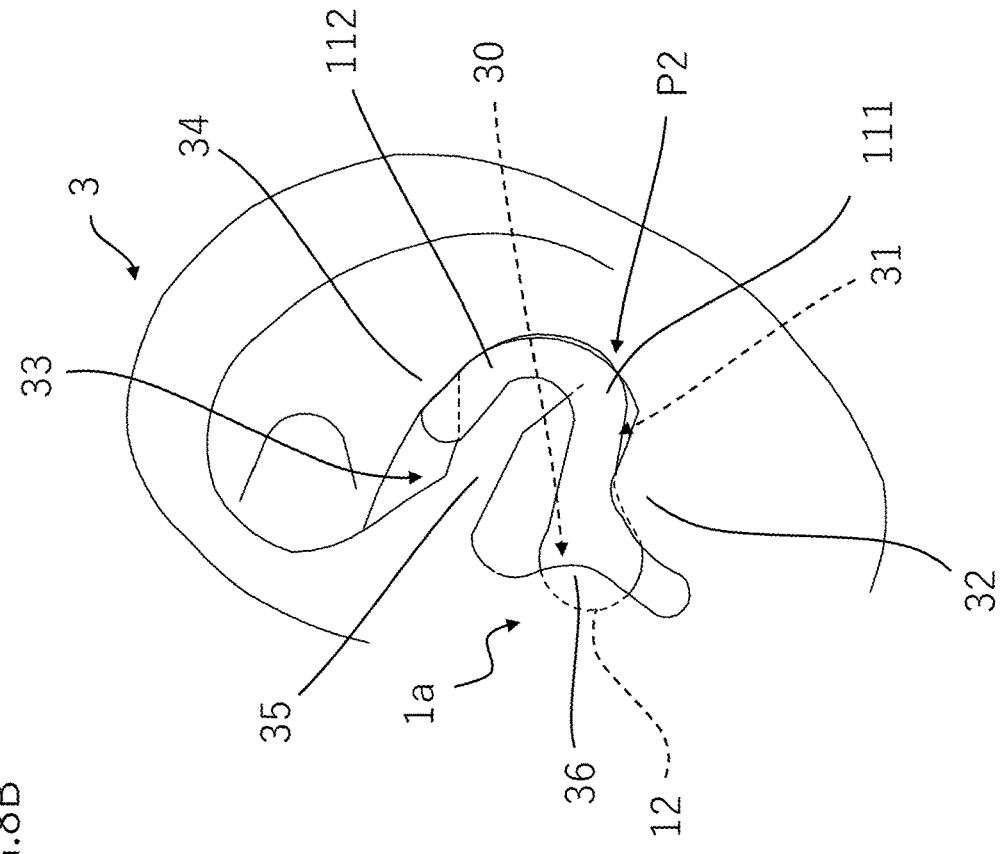
FIG. 8A is a bottom view of an auricle heating device according to another variation.
FIG. 8B is a diagram showing a usage state of the auricle heating device according to the other variation.

FIG. 8A is a bottom view of the holding portion 10 and the fixing portion 11 according to another variation. As shown in FIG. 8A, the holding portion 11 may include a second extension portion 111 that extends from the holding portion 10, in addition to the insertion portion 12. FIG. 8B is a view showing the usage state of the heating device 1a shown in FIG. 8A. As shown in FIG. 8B, the second extension portion 111 extends from the holding portion 10, and reaches a first position P2 that is a position on the inner wall surface of the cavum conchae 31 and is located inward of an antihelix 34. The insertion portion 12 and the second extension portion 111 are configured to press against the inner side of the auricle 3 while the insertion portion 12 uses the inner wall surface of the external acoustic meatus hole 30 as a support portion, and the second extension portion 111 uses the first position P2 as a support portion. Thus, the holding portion 10 is reliably fixed so as to be in contact with the inside of the auricle 3, preferably the cavum conchae 31. Note that the fixing portion 11 may also include a third extension portion 112 that extends from the second extension portion 111 and further along the antihelix 34, straddles the crus helicis 35, and reaches the cymba conchae 33. The heating body 2 is not shown in FIG. 8, but as described above, the shape of and the method of housing the heating body 2 in the holding portion 10 may be selected as necessary.

<4-5>

Figure 9B:
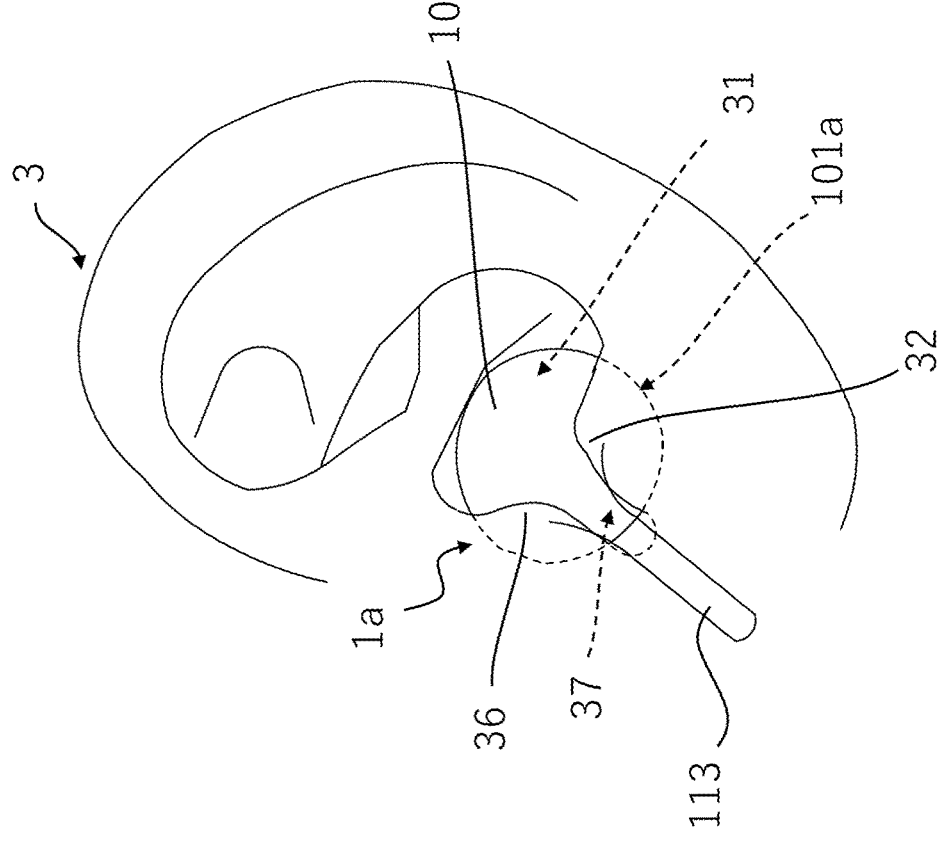
FIG. 9B is a diagram showing a usage state of the auricle heating device according to the further variation.
Figure 9A:
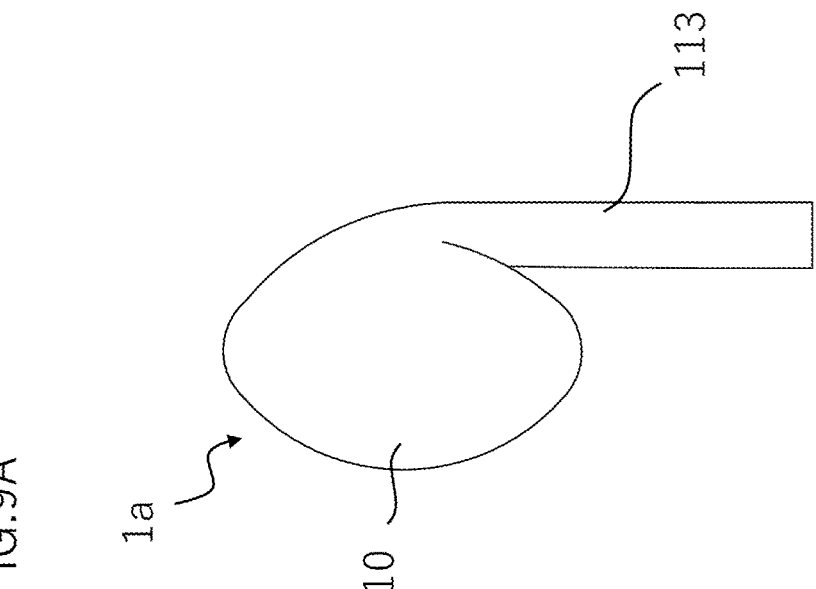
FIG. 9A is a side view of an auricle heating device according to a further variation.

FIG. 9A is a side view of the holding portion 10 and the fixing portion 11 according to a further variation. As shown in FIG. 9A, the fixing portion 11 may include a hooking portion 113 that extends from the outer surface of the holding portion 10 and can be hooked to an intertragic notch 37. FIG. 8B is a diagram showing the usage state of the heating device 1a shown in FIG. 8A. As shown in FIG. 8B, the hooking portion 113 has a substantially columnar shape, and is configured to be hooked to the intertragic notch 37 and extend to the outside of the intertragic notch 37. Thus, the holding portion 10 is reliably fixed so as to be in contact with the inside of the auricle 3, preferably the cavum conchae 31. Note that, as shown in FIG. 9B, the holding portion 10 may be configured to be positioned inward of the antitragus 32 and inward of an antilobium 36. The heating body 2 is not shown in FIG. 9, but as described above, the shape of and the method of housing the heating body 2 in the holding portion 10 may be selected as necessary. Also, the fixing portion 11 may also include the insertion portion 12.

<4-6>

In the embodiment, the heating body 2 is a disposable component that utilizes a metal oxidation reaction, but the principle of heat generation is not limited to this, and the heating body 2 may be a reusable component. The heating body 2 may be, for example, a heat pad that utilizes a supercooling reaction of an aqueous solution of sodium acetate. Also, the heating body 2 may include a substance with high heat storability, and be configured to be used after being heated in hot water, a microwave oven, or the like, or configured to be used after being heated using resistance heat of a current. In light of not needing a separate device for heating the heating body 2 and ease of use, the heating body 2 is preferably a heat pad that generates heat itself.

EXAMPLES

Examples of the present invention are described below. Note that the following examples are merely examples of the present invention and do not limit the present invention.

Experiment Method

Figures 10A, 10B:
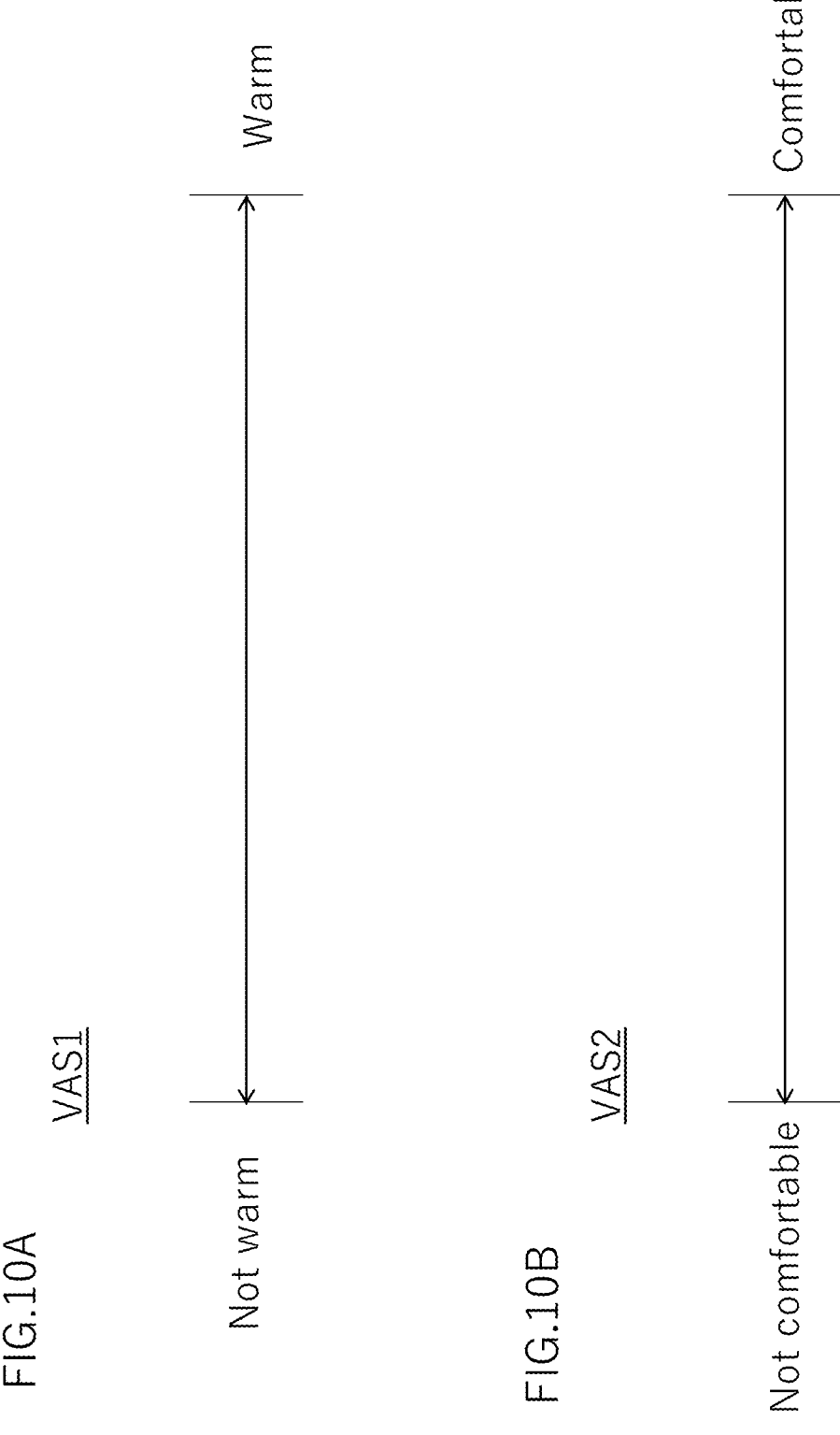
FIG. 10A is a diagram showing a scale used in evaluation of warmth by a subject.
FIG. 10B is a diagram showing a scale used in evaluation of comfort by a subject.

Small heat pads were attached to specific portions of the left and right auricles 3 of 29 subjects, and the degree of "warmth" and "comfort" of each portion to which a small heat pad was attached was denoted in the visual analog scales (VAS) 1 and 2 shown in FIG. 10. The distance between "not warm" and "warm" at two ends of the VAS 1 and the distance between "not comfortable" and "comfortable" at two ends of the VAS 2 respectively indicate 100%, and the measured distance to a position denoted by a subject from "not warm" and "not comfortable" was used to calculate a corresponding percentage with which "warmth" and "comfort" were evaluated.

Each small heat pad had the shape shown in FIG. 3 and the diameter of the flange portion thereof was 26 mm. Each small heat pad was attached to a later-described portion of the auricle 3 using an adhesive sticker. It took approximately one minute for the small heat pads to reach 40° C. with the maximum temperature being 52° C., and temperatures of 40° C. or greater lasted for approximately ten minutes.

11

Figure 11:
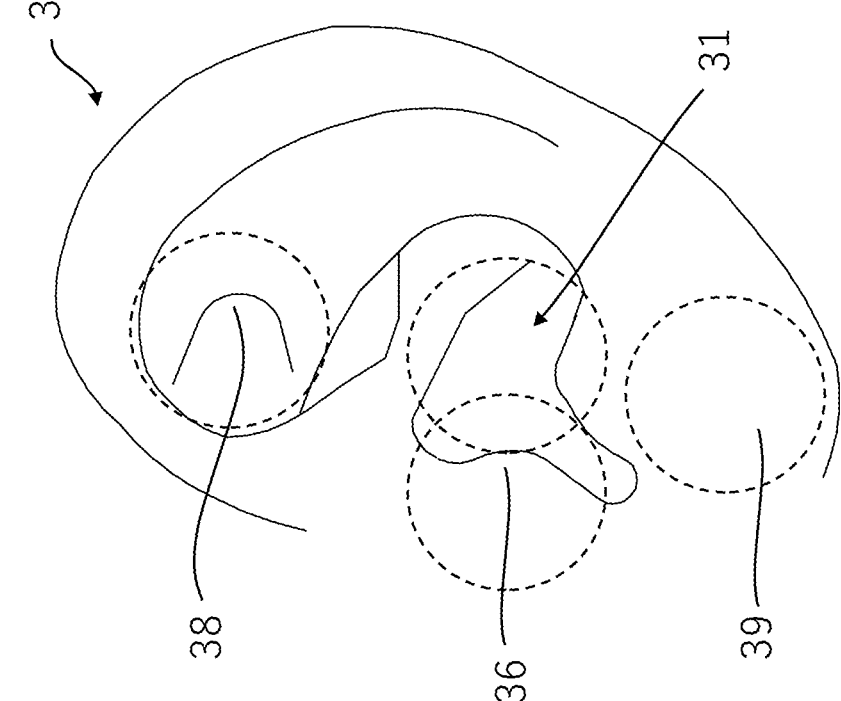
FIG. 11 is a diagram showing portions where a small heat pad was worn in an experiment.

As shown in FIG. 11, the four attachment positions of the small heat pads were:

1) a position centered around an acupuncture point called shenmen 38;
2) the antilobium 36 and surrounding region—a position where blood vessels, nerves, and lymphatic pathways are concentrated;
3) cavum conchae 31—a position where the vagus nerve is located; and
4) an ear lobe 39.

Note that FIG. 11 shows the left auricle 3, but the same also applies to the right auricle 3.

Experiment Results

Figure 12:
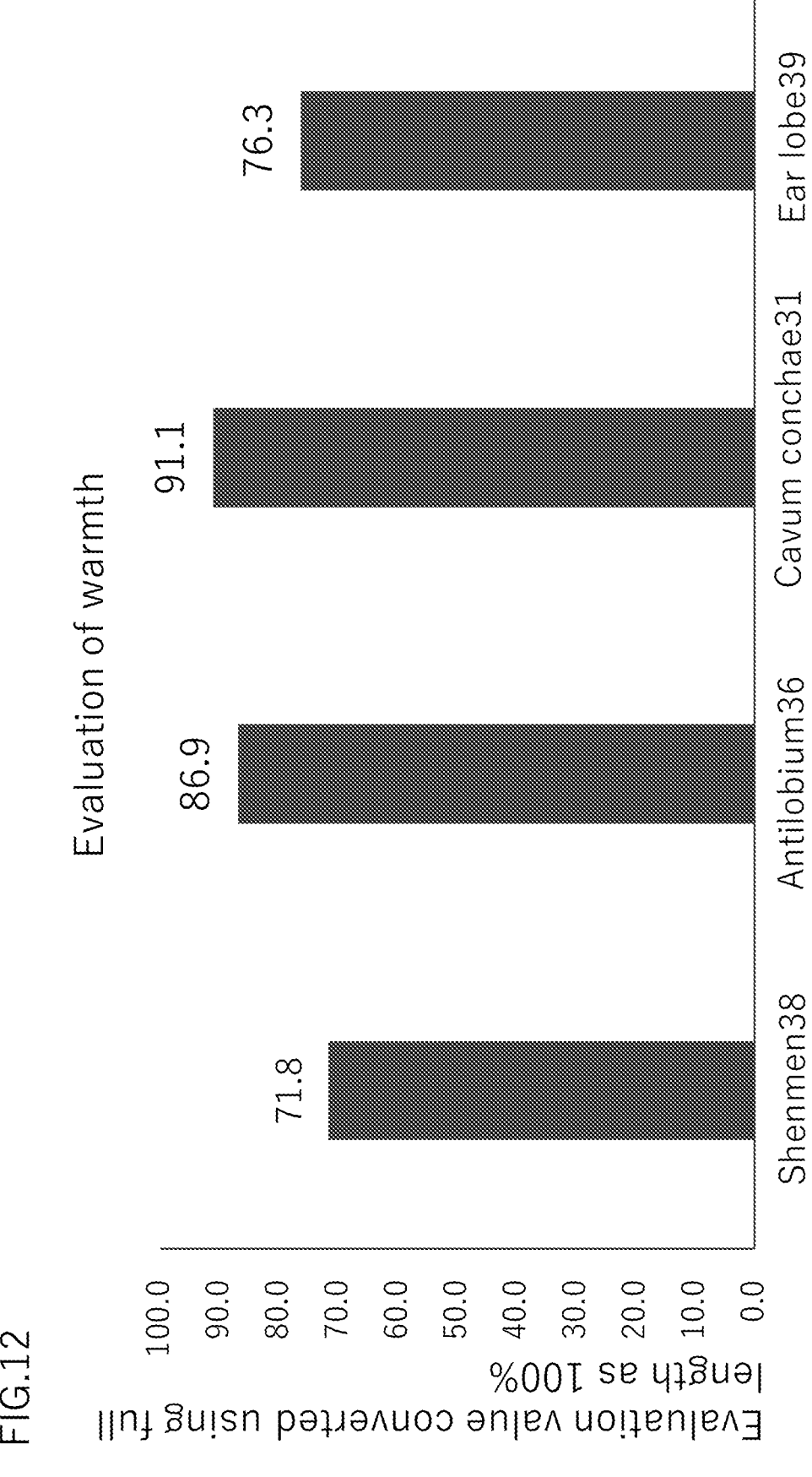
FIG. 12 is a graph showing experiment results.
Figure 13:
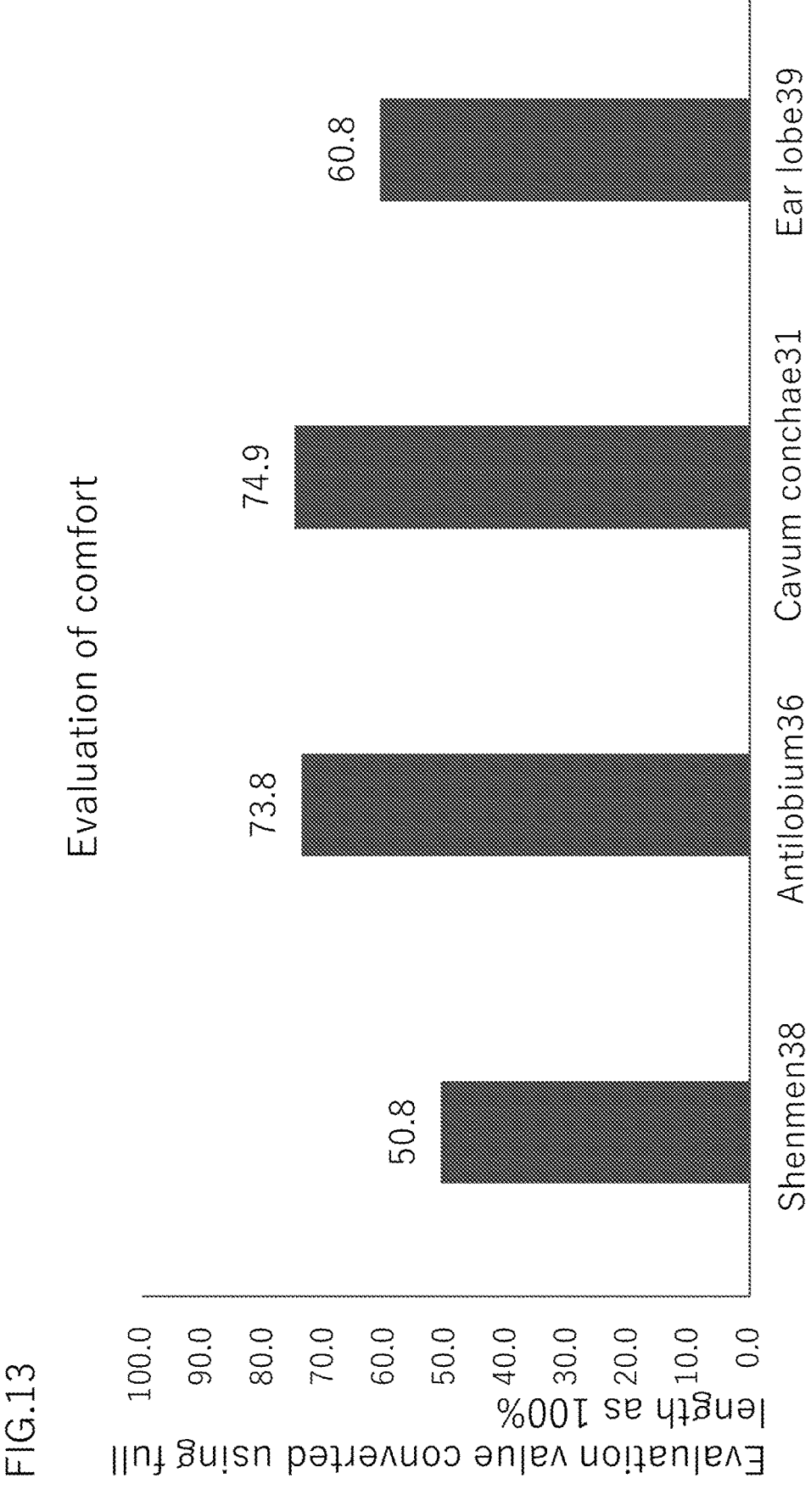
FIG. 13 is a graph showing experiment results.

The averaged results of evaluations of "warmth" and "comfort" at the positions 1) to 4) made by all subjects are as indicated in the graphs shown in FIGS. 12 and 13. Based on these graphs, it can be understood that "warmth" and "comfort" had the highest evaluation average when the cavum conchae 31 was heated. In other words, it is clear that, by disposing the holding portion 10 holding the heating body 2 so as to be centered on the cavum conchae 31, the user can effectively perceive warmth and comfort.

LIST OF REFERENCE NUMERALS

1 Auricle Heating Device
1*a*, 1*b* Heating Device
2 Heating Body
10 Holding Portion
11 Fixing Portion
12 Insertion Portion
100 Contact Surface Portion
100*a* Contact Surface
101 Side Wall Portion
101*a* Supporting portion
110 First Extension Portion
111 Second Extension Portion

The invention claimed is:

1. An auricle heating device comprising a pair of left and right heating devices that are to be respectively worn in a left and right ear,
wherein each heating device includes:
a heating body;
a holding portion configured to hold the heating body; and
a fixing portion that is connected to the holding portion and configured to be worn in an auricle so as to fix the holding portion so as to be in contact with an inner side of the auricle at a predetermined position,
wherein the left and right heating devices are separate from each other, and
wherein, in each heating device,
the fixing portion includes an insertion portion configured to be inserted to a shallow portion of an external acoustic meatus hole while being in intimate contact with an inner wall surface of the external acoustic meatus hole, and
the insertion portion is configured to close off the external acoustic meatus hole and block out external audio.
2. The auricle heating device according to claim 1, wherein, in each heating device,
the fixing portion is worn in the auricle such that the holding portion is fixed so as to be in contact with an inner wall surface near a cavum conchae.

3. The auricle heating device according to claim 2, wherein, in each heating device,
the holding portion includes a supporting portion configured to come in contact with the inner wall surface of the cavum conchae located near an antitragus, and support fixing realized by the fixing portion.
4. The auricle heating device according to claim 1, wherein, in each heating device,
the holding portion includes a contact surface portion that includes a contact surface configured to come into contact with the inner side of the auricle at a predetermined position, and a side wall portion that stands upright from a circumferential edge of the contact surface portion, and
the heating body is fitted into the side wall portion from a back surface side of the contact surface and held by the heating body.
5. The auricle heating device according to claim 3, wherein, in each heating device,
the fixing portion includes a first extension portion that extends from the holding portion and is configured to reach an inner wall surface of a cymba conchae, and
the first extension portion and the supporting portion are configured to press against the inner side of the auricle while the first extension portion uses the inner wall surface of the cymba conchae as a support portion and the supporting portion uses the inner wall surface of the cavum conchae located near the antitragus as a support portion.
6. The auricle heating device according to claim 1, wherein, in each heating device,
the fixing portion includes a second extension portion that extends from the holding portion and is configured to reach a first position that is on an inner wall surface of a cavum conchae and that is located inward of an antihelix, and
the insertion portion and the second extension portion are configured to press against the inner side of the auricle while the insertion portion uses the inner wall surface of the external acoustic meatus hole as a support portion and the second extension portion uses the first position as a support portion.
7. The auricle heating device according to claim 1, wherein, in each heating device,
the fixing portion includes a hooking portion that is to be hooked to an intertragic notch.
8. The auricle heating device according to claim 1, wherein, in each heating device,
the heating body generates heat using a chemical reaction.
9. The auricle heating device according to claim 8, wherein, in each heating device,
the chemical reaction includes a metal oxidation reaction.
10. The auricle heating device according to claim 1, wherein, in each heating device,
the heating body is a disposable component.
11. The auricle heating device according to claim 1, wherein, in each heating device,
at least one of the holding portion and the fixing portion is made of at least one of rubber, elastomer, and a synthetic resin.
12. The auricle heating device according to claim 1, wherein, in each heating device,
at least one of the holding portion and the fixing portion is made of at least one of rubber mixed with a metal, rubber mixed with carbon, an elastomer mixed with a metal, an elastomer mixed with carbon, a synthetic resin mixed with a metal, a synthetic resin mixed with carbon, and a thermally conductive resin.

13. The auricle heating device according to claim 2, wherein, in each heating device, the holding portion includes a contact surface portion that includes a contact surface configured to come into contact with the inner side of the auricle at a predetermined position, and a side wall portion that stands upright from a circumferential edge of the contact surface portion, and the heating body is fitted into the side wall portion from a back surface side of the contact surface and held by the heating body.

14. The auricle heating device according to claim 2, wherein, in each heating device, the fixing portion includes an insertion portion configured to be inserted to a shallow portion of an external acoustic meatus hole while being in intimate contact with an inner wall surface of the external acoustic meatus hole.

15. The auricle heating device according to claim 2, wherein, in each heating device, the heating body generates heat using a chemical reaction.

16. The auricle heating device according to claim 15, wherein, in each heating device, the chemical reaction includes a metal oxidation reaction.

17. The auricle heating device according to claim 2, wherein, in each heating device, the heating body is a disposable component.

18. The auricle heating device according to claim 2, wherein, in each heating device, at least one of the holding portion and the fixing portion is made of at least one of rubber, elastomer, and a synthetic resin.

19. An auricle heating device comprising a pair of left and right heating devices that are to be respectively worn in a left and right ear, wherein each heating device includes:

a heating body;

a holding portion configured to hold the heating body; and a fixing portion that is connected to the holding portion and configured to be worn in an auricle so as to fix the holding portion so as to be in contact with an inner side of the auricle at a predetermined position, and the left and right heating devices are separate from each other, the holding portion is made of a flexible material and includes a space into which the heating body is fitted, and the heating body is held within by deformation of the space.

* * * * *